United States Patent
Gambale et al.

(10) Patent No.: US 6,692,520 B1
(45) Date of Patent: *Feb. 17, 2004

(54) SYSTEMS AND METHODS FOR IMBEDDED INTRAMUSCULAR IMPLANTS

(75) Inventors: Richard A. Gambale, Tyngsboro, MA (US); Mike Weiser, Groton, MA (US); Stephen Forcucci, Arlington, MA (US); Chirag B. Shah, Nashua, NH (US)

(73) Assignee: C. R. Bard, Inc., Murray Hill, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/211,332

(22) Filed: Dec. 15, 1998

(51) Int. Cl.$^7$ .................................................. A61F 2/06
(52) U.S. Cl. .................... 623/1.1; 623/11.11; 623/23.72
(58) Field of Search ............................... 623/1.1, 1.12, 623/1.15, 11.11, 14.13, 23.72; 128/898, 899

(56) References Cited

U.S. PATENT DOCUMENTS

| | | | |
|---|---|---|---|
| 3,991,750 A | 11/1976 | Vickery | |
| 3,995,617 A | 12/1976 | Watkins et al. | |
| 4,307,722 A | 12/1981 | Evans et al. | |
| 4,503,569 A | 3/1985 | Dotter | |
| 4,546,499 A | 10/1985 | Possis | |
| 4,562,597 A | 1/1986 | Possis et al. | |
| 4,580,568 A | 4/1986 | Gianturco | |
| 4,582,181 A | 4/1986 | Samson | |
| 4,641,653 A | 2/1987 | Rockey | |
| 4,649,922 A | 3/1987 | Wiktor | |
| 4,655,771 A | 4/1987 | Wallsten | |
| 4,658,817 A | 4/1987 | Hardy et al. | |
| 4,665,918 A | 5/1987 | Garza et al. | |
| 4,681,110 A | 7/1987 | Wiktor et al. | |
| 4,718,425 A | 1/1988 | Tamaka et al. | |
| 4,733,665 A | 3/1988 | Palmaz | |
| 4,768,507 A | 9/1988 | Fischell et al. | |
| 4,774,949 A | 10/1988 | Fogarty | |
| 4,785,815 A | 11/1988 | Cohen | |

(List continued on next page.)

FOREIGN PATENT DOCUMENTS

| | | |
|---|---|---|
| DE | 19703482 | 1/1997 |
| DE | 296 19 029 u1 | 4/1997 |
| EP | 0 132 387 | 1/1985 |
| EP | 0 363 661 | 4/1990 |
| EP | 0 515 867 A2 | 12/1992 |

(List continued on next page.)

OTHER PUBLICATIONS

Neil B. Ingels, et al., Measurement of Midwall Myocardial Dynamics in Intact Man by Radiography of Surgically Implanted Markers, Circulation, vol. 52, pp. 859–867 (Nov. 1975).

A. Sachinopoulou et al., "Invited Review Transmyocardial Revascularization", Lasers in Medical Science 1995, vol. 10, pp. 83–91, Sep. 1995.

(List continued on next page.)

*Primary Examiner*—Dinh X. Nguyen

(57) ABSTRACT

The invention includes systems and methods for stimulating intramuscular angiogenesis by placing a biocompatible device within the tissue of a muscle. The biocompatible device is dimensionally adapted for placement within the tissue of a muscle. Placement of the biocompatible device within the muscle can take place according to the method of the invention by using techniques familiar to those of ordinary skill in the art. Illustrative techniques for placement of the device within the myocardium comprise one practice of the method of the invention.

9 Claims, 9 Drawing Sheets

U.S. PATENT DOCUMENTS

| | | |
|---|---|---|
| 4,813,925 A | 3/1989 | Anderson, Jr. et al. |
| 4,852,580 A | 8/1989 | Wood |
| 4,861,330 A | 8/1989 | Voss |
| 4,904,264 A | 2/1990 | Scheunemann |
| 4,917,666 A | 4/1990 | Solar et al. |
| 4,920,980 A | 5/1990 | Jackowski |
| 4,950,227 A | 8/1990 | Savin et al. |
| 4,995,857 A | 2/1991 | Arnold |
| 4,997,431 A | 3/1991 | Isner et al. |
| 5,040,543 A | 8/1991 | Badera et al. |
| 5,042,486 A | 8/1991 | Pfeiler et al. |
| 5,047,028 A | 9/1991 | Gian |
| 5,049,138 A | 9/1991 | Chevalier et al. |
| 5,056,517 A | 10/1991 | Fenici |
| 5,087,243 A | 2/1992 | Avitall |
| 5,098,374 A | 3/1992 | Othel-Jacobsen et al. |
| 5,114,414 A | 5/1992 | Buchbinder |
| 5,158,548 A | 10/1992 | Lau et al. |
| 5,167,614 A | 12/1992 | Tessman et al. |
| 5,172,699 A | 12/1992 | Svenson |
| 5,176,626 A | 1/1993 | Soehendra |
| 5,180,366 A | 1/1993 | Woods |
| 5,190,058 A | 3/1993 | Jones et al. |
| 5,256,146 A | 10/1993 | Ensminger et al. |
| 5,266,073 A | 11/1993 | Wall |
| 5,287,861 A | 2/1994 | Wilk |
| 5,290,295 A | 3/1994 | Querals et al. |
| 5,312,456 A | 5/1994 | Reed et al. |
| 5,324,325 A | 6/1994 | Moaddeb |
| 5,366,493 A | 11/1994 | Scheiner et al. |
| 5,372,600 A | 12/1994 | Beyar et al. |
| 5,380,316 A | 1/1995 | Aita et al. |
| 5,386,828 A | 2/1995 | Owens et al. |
| 5,389,096 A | 2/1995 | Aita et al. |
| 5,391,199 A | 2/1995 | Ben-Haim |
| 5,409,004 A | 4/1995 | Sloan |
| 5,409,019 A | 4/1995 | Wilk |
| 5,423,885 A | 6/1995 | Williams |
| 5,425,757 A | 6/1995 | Tiefenbrun et al. |
| 5,429,144 A | 7/1995 | Wilk |
| 5,441,516 A | 8/1995 | Wang et al. |
| 5,452,733 A | 9/1995 | Sterman |
| 5,453,090 A | 9/1995 | Martinez et al. |
| 5,458,615 A | 10/1995 | Klemm |
| 5,464,404 A | 11/1995 | Abela et al. |
| 5,464,650 A | 11/1995 | Berg et al. |
| 5,466,242 A | 11/1995 | Mori |
| 5,476,505 A | 12/1995 | Limon |
| 5,480,422 A | 1/1996 | Ben-Halm |
| 5,487,739 A | 1/1996 | Aebischer et al. |
| 5,514,176 A | 5/1996 | Bosley, Jr. et al. |
| 5,551,954 A | 9/1996 | Buscemi et al. |
| 5,558,091 A | 9/1996 | Acker et al. |
| 5,562,619 A | 10/1996 | Mirarchi et al. |
| 5,562,922 A | 10/1996 | Lambert |
| 5,569,272 A | 10/1996 | Reed |
| 5,571,168 A | 11/1996 | Toro |
| 5,593,412 A | 1/1997 | Martinez et al. |
| 5,593,434 A | 1/1997 | Williams |
| 5,602,301 A | 2/1997 | Field |
| 5,614,206 A | 3/1997 | Randolph et al. |
| 5,643,308 A | 7/1997 | Markman |
| 5,653,756 A | 8/1997 | Clarke et al. |
| 5,655,548 A | 8/1997 | Nelson |
| 5,662,124 A | 9/1997 | Wilk |
| 5,676,850 A | 10/1997 | Reed et al. |
| 5,690,643 A | 11/1997 | Wijay |
| 5,713,894 A | 2/1998 | Murphy-Chutorian et al. ............ 606/15 |
| 5,724,975 A | 3/1998 | Negus et al. .......... 128/661.09 |
| 5,725,521 A | 3/1998 | Mueller .......................... 606/7 |
| 5,725,523 A | 3/1998 | Mueller ....................... 606/15 |
| 5,735,897 A | 4/1998 | Buirge |
| 5,741,330 A | 4/1998 | Brauker et al. |
| 5,744,515 A | 4/1998 | Clapper |
| 5,755,682 A | 5/1998 | Knudson et al. |
| 5,756,127 A | 5/1998 | Grisoni et al. |
| 5,769,843 A | 6/1998 | Abela et al. |
| 5,782,823 A | 7/1998 | Mueller |
| 5,785,702 A | 7/1998 | Murphy et al. |
| 5,792,453 A | 8/1998 | Hammond et al. |
| 5,797,870 A | 8/1998 | March et al. |
| 5,807,384 A | 9/1998 | Mueller |
| 5,810,836 A | 9/1998 | Hussein |
| 5,817,101 A | 10/1998 | Fiedler |
| 5,824,049 A | 10/1998 | Ragheb et al. |
| 5,824,071 A | 10/1998 | Nelson et al. |
| 5,830,502 A | 11/1998 | Dong et al. |
| 5,833,608 A | 11/1998 | Acker |
| 5,840,059 A | 11/1998 | March et al. |
| 5,861,032 A | 1/1999 | Subramaniam |
| 5,879,383 A | 3/1999 | Bruchman et al. |
| 5,971,993 A | 10/1999 | Hussein et al. |
| 5,980,514 A | 11/1999 | Kupiecki et al. |
| 5,980,548 A | 11/1999 | Evans et al. |
| 6,045,565 A | 4/2000 | Ellis et al. |
| 6,263,880 B1 | 7/2001 | Parker et al. |
| 6,432,126 B1 * | 8/2002 | Gambale et al. ............. 623/1.1 |

FOREIGN PATENT DOCUMENTS

| | | |
|---|---|---|
| EP | 0 714 640 A1 | 6/1996 |
| EP | 0 717 969 A2 | 6/1996 |
| EP | 0 732 089 A2 | 9/1996 |
| EP | 0 876 803 A2 | 11/1996 |
| EP | 0 207 438 | 1/1997 |
| EP | 0 797 957 | 10/1997 |
| EP | 0 797 958 | 10/1997 |
| EP | 0 807 412 | 11/1997 |
| EP | 0 807 417 | 11/1997 |
| EP | 0 812 574 | 12/1997 |
| EP | 0 812 574 A2 | 12/1997 |
| EP | 0 815 798 | 1/1998 |
| EP | 0 830 873 A2 | 3/1998 |
| EP | 0 853 921 A2 | 7/1998 |
| EP | 0 953 320 A2 | 11/1999 |
| FR | 1.278.965 | 1/1961 |
| FR | 1.514.319 | 1/1967 |
| FR | 1514319 | 1/1967 |
| RU | 2026640 C1 | 1/1995 |
| RU | 2063179 C1 | 7/1996 |
| WO | WO 89/01798 | 3/1989 |
| WO | WO 91/15254 | 10/1991 |
| WO | WO 94/05265 | 3/1994 |
| WO | WO 94/27612 | 12/1994 |
| WO | WO 95/33511 | 12/1995 |
| WO | WO 96/20698 | 7/1996 |
| WO | WO 97/42910 | 7/1997 |
| WO | WO 97/32551 | 9/1997 |
| WO | WO 97/34540 | 9/1997 |
| WO | WO 97/38730 | 10/1997 |
| WO | WO 97/45105 | 12/1997 |
| WO | WO 97/47253 | 12/1997 |
| WO | WO 98/05307 | 2/1998 |
| WO | WO 98/08456 | 3/1998 |
| WO | WO 98/16644 | 4/1998 |
| WO | WO 98/23228 | 6/1998 |
| WO | WO 98/25533 | 6/1998 |
| WO | WO 98/29148 | 7/1998 |
| WO | WO 98/32859 | 7/1998 |
| WO | WO 98/46115 | 10/1998 |
| WO | WO 99/21510 | 5/1999 |

| | | |
|---|---|---|
| WO | WO 99/38459 | 8/1999 |
| WO | WO 99/53863 | 10/1999 |

OTHER PUBLICATIONS

B. Schumacher et al., "Induction of Neoangiogenesis in Ischemic Myocardium by Human Growth Factors, First Clinical Results of A New Treatment of Coronary Heart Disease", Clinical Investigation and Reports, pp. 645–650, Dec. 1997.

Garrett Lee et al., "Feasibility of Intravascular Laser Irradiation for in Vivo Visualization and Therapy of Cardiocirculatory. Diseases", American Heart Journal, vol. 103 No. 6, pp. 1076–1077.

Garrett Lee et al., "Laser–Dissolution of Coronary Atherosclerotic Obstruction", American Heart Journal, vol. 102, No. 6, part 1, pp. 1074–1075, Dec. 1981.

George S. Abela et al., "Use of Laser Radiation to Recanalize Totally Obstructed Coronary Arteries (Abstract)", Journal American College Cardiology 1983:1(2):691.

George S. Abela et al., "Laser Revascularization: What are Its Prospects?", Journal of Cardiovascular Medicine, pp. 977–984, Sep. 1983.

Isam N. Anabtawi et al., "Experimental Evaluation of Myocardial Tunnelization as a Method of Myocardial Revascularization, Journal of Thoracic and Cardiovascular Surgery", vol. 58, No. 5, pp. 638–646, Nov. 1969.

John E. Hershey et al., "Transmyocardial Puncture Evascularization", Geriatrics, pp. 101–108, Mar. 1969.

M. A. Martinelli, et al., "Intraluminal Ultrasound Guidance of Transverse Laser Coronary Atherectomy", Optical Fibers in Medicine vol. 1201, pp. 68–78, (1990).

Mahmood Mirhoseini et al., "Transventricular Revascularization by Laser", Lasers in Surgery and Medicine, vol. 2, pp. 187–198, 1982.

Mahmood Mirhoseini et al., "Clinical Report: Laser Myocardial Revascularization", Lasers in Surgery and Medicine vol. 6, pp. 459–461, 1986.

Mahmood Mirhoseini et al., "New Concepts in Revascularization of the Myocardium", The Annals of Thoracic Surgery, vol. 45, No. 4, pp. 415–420, Apr. 1988.

Peter Whittaker, et al., "Transmural Channels Can Protect Ischemic Tissue, Assessment of Long–Term Myocardial Response to Laser and Needle–Made Channels", Circulation, vol. 93, No. 1, pp. 143–152, Jan. 1996.

P.K. Sen, et al, "Further Studies in Multiple Transmyocardial Acupuncture as a Method of Myocardial Revascularization", Surgery, vol. 64, No. 5, pp. 861–870, Nov. 1968.

R.I. Hardy et al., "Regional Myocardial Blood Flow and Cardiac Mechanics in Dog Hearts with $CO_2$ Laser–Induced Intramyocardial Revascularization", Basic Research Cardiology, 85:179–197 (1990).

Roque Pifarre et al., "Myocardial Revascularization by Transmyocardial Acupuncture: A Physiologic Impossibility; Journal of Thoracic and Cardiovascular Surgery"; vol. 58, No. 3, pp. 424–429, Sep. 1969.

A. Hassan Khazei et al., "Myocardial Canalization: A New Method of Myocardial Revascularization", The Annals of Thoracic Surgery, vol. 6, No. 2, Aug. 1968, pp. 163–171.

Alfred Goldman et al., "Experimental Methods for Producing a Collateral Circulation to the Heart Directly from the Left Ventricle", J. Thoracic Surg. Mar. 1956; vol. 31., No. 5, pp. 364–374.

C. Massimo et al. "Myocardial Revascularization by a New Method fo Carrying Blood Directly From the Left Ventricular Cavity Into the Coronary Circulation", J. Thoracic Surg., Aug. 1957, vol. 34, No. 2, pp. 257–264.

Charles T. Doiter, "Transluminally–Placed Coilsping Endarterial Tube Grafts", Sep.–Oct. 1969, vol. 4, pp. 329–332.

M. Mirhoseini et al., "Revascularization of the Heart by Laser", Journal of Microsurgery, Jun. 1981, Journal of Microsurgery, Jun. 1981, pp. 253–260.

P. Walter et al., "Treatment of Acute Myocardial Infarction by Transmural Blood Supply from the Venticular Cavity", Europ. Surg. Res. 3:130–138 (1971).

P.K. Sen et la., "Transmyocardial Acupuncture: A New Approach to Myocardial Revascularization", Journal of Thoracic and Cardiovascular Surgery, vol. 50, No. 2, Aug. 1965, pp. 181–189.

M. Mirhoseini et al., Revascularization of the Heart by Laser, Journal of Microsurgery, Jun. 1981, pp. 253–260.

Valluvan Jeevanandam et al., "Myocardial Revascularization by Laser–Induced Channels", Surginal Forum, pp. 225–227.

S. Banai et al., "Angiogenic–Induced Enhancement of Collateral Blood Flow to Ischemic Myocardium by Vascular Endothelial Growth Factor in Dogs," Circ. vol. 89, No. 5, pp. 2183–2189 (May 1994).

M. Bevans and E. McLimore, "Intracoronary stents: A new approach to coronary artery dilation," J. Cardiovasc Nurs., pp. 34–49 (Nov. 1992).

C. Chamberlain, "High–Tech for the Heart," ABC News, Internet address abcnews.com/sections/living/hightech1113, pp. 1–4, (Nov. 1997).

R. Favaloro, "Saphenous Vein Autograft Replacement of Severe Segmental Coronary Artery Occlusion," Anals of Thoracic Surg., vol. 5, No. 4, pp. 334–339 (Apr. 1968).

J. Folkman, "Angiogenic Therapy of the Human Heart," Amer. Heart Assoc. Editorial, (Circulation. 1998;97:628–629).

S. Frandzel, "The Perforated Heart," Amer. Health, pp. 11–12 (Dec. 1993).

A. Goldman et al., "Experimental Methods for Producing a Colalteral Circulation to the Heart Directly from the Left Ventricle," J. Thoracic Surg., vol. 31, No. 3, pp. 364–374 (Mar. 1956).

R. Hartman and P. Whittaker, "The Physics of Transmyocardial Laser Revascularization," J. Clin. Laser Med. & Surg., vol. 15, No. 6, pp. 255–259 (1997).

K. Horvath, "Clinical Studies of TMR with the $CO_2$ Laser," J. of Clin. Laser, Med. & Surg., vol. 15, No. 6, pp. 281–285 (1997).

V. Jeevanandam et al., "Myocardial Revascularization by Laser–Induced Channels," Cardiothoracic Surg., pp. 225–226.

A.H. Khazei et al., "Myocardial Canalization, A New Method of Myocardial Revascularization" Annals of Thoracic Surg., vol. 6, No. 2, pp. 163–171 (Aug. 1968).

C. Kim and S. Oesterle, "Percutaneous Transmyocardial Revascularization," J. Clin. Laser Med. & Surg., vol. 15, No. 6, pp. 293–298 (1997).

R. Kuntz et al., "Novel Approach to the Analysis of Restenosis After the Use of Three New Coronary Devices," JACC, vol. 19, No. 7, pp. 1493–1499 (Jun. 1992).

K. Kwong et al., "Transmyocardial Laser Treatment Denervates Canine Myocardium," J. Thoracic Surg., vol. 114, No. 6, pp. 883–890, (Dec. 1997).

R. Lanzafame, "Louisiana Leapers," *J. Clinical Laser Med. & Surg.*, vol. 15, No. 6, p. 241, (1997).

C. Mack et al., "Myocardial Angiogenesis as a Possible Mechanism," *J. Clinical Laser Med. & Surg,* vol. 15, No. 6, pp. 275–279 (1997).

R. March, "Transmyocardial Laser Revascularizatin: Current Experience and Future Direction," *J. Clinical Laser Med. & Surg.,* vol. 15, No. 6, pp. 301–306 (1997).

C. Massimo et al., "Myocardial Revascularization by a New Method of Carrying Blood Directly from the Left Ventricular Cavity into the Coronary Circulation," *J. Thoracic Surg.,* pp. 257–264 (1956).

S. Mehta and W. Pae, Jr., "Complications of Cardiac Surgery," *Cardiac Surgery in the Adult,* Chapt. 13, pp. 369–402.

M. Mirhoseini and M. Cayton, "Revascularization of the Heart by Laser," *J. Microsurgery,* vol. 2, pp. 253–260 (1981).

M. Mirhoseini et al., "Myocardial Revascularization by Laser: A Clinical Report," *Lasers in Surgery and Medicine,* vol. 3, pp. 241–245 (1983).

M. Mirhoseini et al., "Transmyocardial Laser Revascularization," *JACC* Abstract No. 959–47, p. 416A (Feb. 1994).

M. Mirhoseini and M. Cayton, "Transmyocardial Laser Revascularization: Historical Background and Future Directions," *J. Clinical Laser Med. & Surg.,* vol. 15, No. 6, pp. 245–253 (1997).

A. Obergfell et al., "Transmyocardial Laser Revascularization (TMLR): Relief of angina and increase in treadmill exercise testing in patients with severe symptomatic angina," Abstract, p. 325.

R. Riessen and J. Isner, "Prospects for Site–Specific Delivery of Pharmacologic and Molecular Therapies," *JACC,* vol. 23, No. 5, pp. 1234–1244 (Apr. 1994).

T. Rosengart, "Transmyocardial Laser Revascularization—A Technique in Evolution," *J. Clinical Laser Med. & Surg.,* vol. 15, pp. 299–300 (1997).

T. Sanborn, "Cardiovascular Applications of Lasers: Searching for a Niche," *J. Clinical Laser Med. & Surg.,* vol. 15, No. 6, pp. 243–244 (1997).

B. Schumacher et al., "Induction of Neoangiogenesis in Ischemic Myocardium by Human Growth Factors, First Clinical Results of a New Treatment of Coronary Heart Disease," *Clinical Investigation and Reports,* pp. 645–650 (1997).

T. Spanier et al., "Angiogenesis: A Possible Mechanism Underlying the Clinical Benefits of Transmyocardial Laser Revascularization," *J. Clinical Laser Med. & Surg.,* vol. 15, No. 6, pp. 269–273 (1997).

T. Spanier et al., "Role for Holmium: YAG Lasers in Transmyocardial Laser Revascularization," *J. Clinical Laser Med. & Surg.,* vol. 15, pp. 287–291 (1997).

R. Spencer, "Clinical Experience with Thoracoscopic TMR Versus Minimally Invasive Approach," *Ann. Thorac. Surg.,* vol. 65, pp. 596–605, (1998).

A.M. Vineberg, "Development of an Anastomosis Between the Coronary Vessels and a Transplanted Internal Mammary Artery," *Canad. M.A.J.,* vol. 55, pp. 117–119 (Aug. 1946).

A. Vineberg, "Coronary Vascular Anastomoses by Internal Mammary Artery Implantation," *Canad. M.A.J.,* vol. 78, pp. 871–879 (Jun. 1958).

B. Waller, "Anatomy, Histology, and Pathology of the Major Epicardial Coronary Arteries Relevant to Echocardiographic Imaging Techniques," *J. Amer. Soc. Echocardiography,* vol. 2, No. 4, pp. 232–252.

P. Walter, "Treatment of Acute Myocardial infarction by Transmural Blood Supply from the Ventricular Cavity," *Europ. Surg. Res.,* vol. 3, pp. 130–138 (1971).

J. Wearn et al., "The Nature of the Vascular Communications Between the Coronary Arteries and the Chambers of the Heart," *Am. Heart J.,* vol. IX, No. 2, pp. 143–164.

P. Whittaker et al., "Laser–Mediated Transmural Myocardial Channels Do Not Salvage Acutely Ischemic Myocardium," *JACC,* vol. 22, No. 1, pp. 302–309 (Jul. 1993).

P. Whittaker, "Detection and Assessment of Laser–Mediated Injury in Transmyocardial Revascularization," *J. Clinical Laser Med. & Surg.,* vol. 15, No. 6, pp. 261–267 (1997).

P. Whittaker, et al., "Transmural Channels Can Protect Ischemic Tissue," *Circ.,* vol. 93, No. 1., pp. 143–152 (Jan. 1996).

R. Wilensky et al., "Methods and Devices for Local Drug Delivery in Coronary and Peripheral Arteries," *TCM,* vol. 3, No. 5, pp. 163–170 (1993).

\* cited by examiner

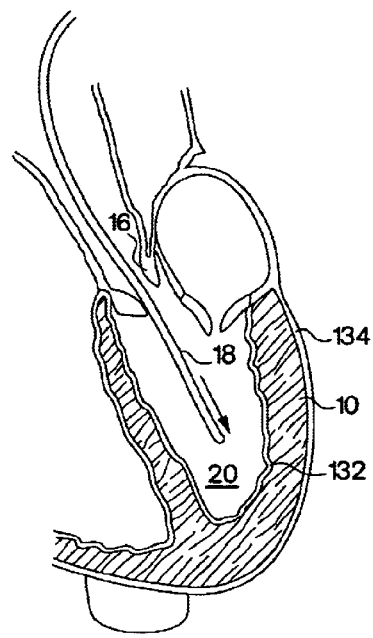 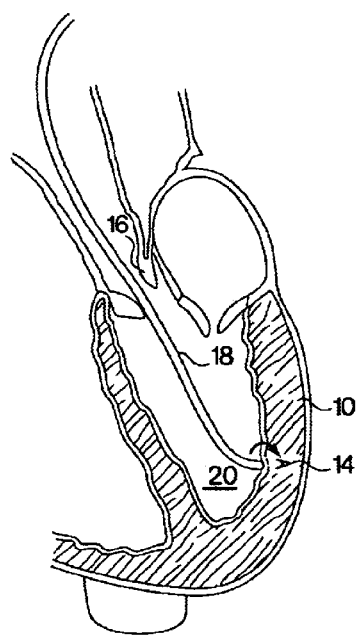
Fig. 7a        Fig. 7b
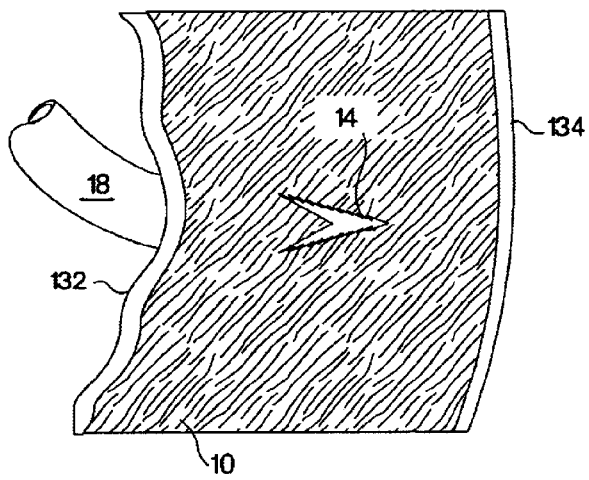 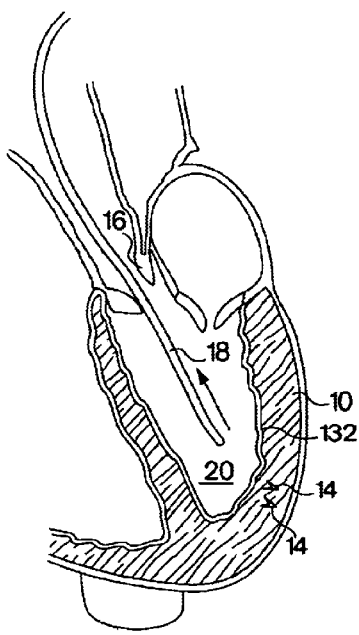
Fig. 7c        Fig. 7d

SYSTEMS AND METHODS FOR IMBEDDED INTRAMUSCULAR IMPLANTS

TECHNICAL FIELD

This invention relates to systems and methods for treating muscle ischemia.

BACKGROUND OF THE INVENTION

To function normally, muscle tissue requires adequate circulatory perfusion. With increases in muscle work, there is an increased demand for blood flow. When arterial inflow is compromised by peripheral vascular disease, this demand cannot be met. The resultant muscle ischemia leads to a syndrome of muscle pain termed claudication. Lower extremities are most commonly affected with peripheral vascular disease and concomitant claudication. Symptoms may abate with sufficient rest, but may then resume with further exertion. Claudication thus can be debilitating. If there is sufficient ongoing muscle ischemia, pain symptoms do not abate with cessation of exertion; the patient then experiences extremity pain at rest. As vascular disease advances, with progressive decrease in arterial inflow, circulation becomes inadequate to support tissue metabolism even at rest. At this point, frank tissue death ensues, including muscle necrosis. Pharmacological treatment offers only minimal palliation of this inexorable process. Surgical intervention through successful arterial revascularization is required before the onset of tissue death if lower extremity amputation is to be avoided.

Acute vascular compromise can also result in tissue necrosis. Embolic phenomena or traumatic injury may occlude major arteries, causing acute ischemia. Emergent surgical intervention is required to prevent catastrophic tissue loss distal to the occlusion. Acute muscle ischemia also occurs following non-vascular trauma. The most common instance of this type of ischemic insult is found in compartment syndromes of the extremities. Compartment syndrome takes place when an injured muscle begins to swell but is restricted in its expansion by some type of local or circumferential compression. Compression may be applied externally, for example by a cylindrical cast or a dressing that is tightly applied, or compression may be applied internally by the fascia covering the muscles within an extremity compartment. The result of a compartment syndrome is some degree of ischemic damage to the muscle, culminating in frank muscle necrosis if the ischemia persists long enough. Treatment of compartment syndromes requires relief of external circumferential compression and release of anatomical compression through surgery. Release of the confining anatomic structures may entail longitudinal incisions in both the skin and the muscular fascia. Even after adequate compartment release, the local ischemia and its sequelae must resolve over time as the compartment pressures and the intravascular perfusion pressures reach a more physiological equilibrium. During this period, further tissue damage may occur, with subsequent functional effects. No specific therapeutic interventions exist to decrease the extent of ischemic damage to muscle tissue following restoration of effective circulation. One example of the outcome of extensive muscle necrosis is Volkmann's ischemic contracture, a condition that results from the death of the forearm flexor wad muscles following a forearm compartment syndrome: a patient afflicted with Volkmann's ischemic contracture positions the wrist and fingers in a permanently flexed position due to the contracture of the damaged muscle mass, and the patient loses the ability either to flex or to extend the wrist or the fingers.

Muscle ischemia, when it occurs in the muscle of the myocardium, leads to similar symptoms of muscle pain and local muscle death and dysfunction. Myocardial ischemia is well-known to lead to angina pectoris and myocardial infarction, disorders that can be debilitating and life-threatening. The American Heart Association estimates that these disorders afflict more than six million people (American Heart Association, *Heart and Stroke Facts,* 1994 Statistical Supplement (Dallas: American Heart Association, 1994)). All these conditions entail a mismatch between coronary blood inflow and myocardial oxygen demand. Medical therapies have been developed to alter the demand side of this equation, reducing cardiac preload, afterload, heart rate and contractility. In addition, thrombolytic therapies are available in the setting of acute myocardial infarction to effect restoration of interrupted local blood flow. However, despite the medical interventions that have evolved to treat or palliate the consequences of ischemic heart disease, morbidity and mortality remain substantial.

In cases of life-threatening ischemia, or in cases that have been refractory to medical management, more invasive intervention is required. Available modalities include surgery and percutaneous transluminal coronary angioplasty (PTCA), both designed to improve the supply side of the inflow/demand equation. The predominant surgical procedure, since its introduction by Favaloro in 1967, (R. Favaloro, "Saphenous vein autograft replacement of severe segmental coronary artery occlusion: Operative technique," *Ann. Thor. Surg.* 5:334, 1968) is the coronary artery bypass graft (CABG) operation. Coronary artery bypass grafts, using the patient's native veins or arteries, are conduits that bring blood from vessels proximal to a coronary vascular obstruction to the distal coronary artery. This procedure is long and technically complicated, with a prolonged convalescence and an extensive list of potential complications (S. Mehta and W. Pae, "Complications of cardiac surgery," pp. 369–402 in *Cardiac Surgery in the Adult,* ed. L E Edmunds (New York: McGraw-Hill, 1997)). The operation usually requires cardiopulmonary bypass, with its own set of risks. Surgical access is through a thoracotomy or, more commonly, a median sternotomy; both access routes are associated with post-operative pain, atelectasis and wound healing problems.

Today, several hundred thousand CABG procedures are performed annually. Survival benefit has been described in patients with higher risk disease, and relief of symptoms occurs in 80–90% of patients for whom medical management had proven inadequate (Yusef et al., "Effect of coronary artery bypass graft surgery on survival: Overview of ten-year results from randomized trials by the Coronary Artery Bypass Graft Surgery Trialist Collaboration," *Lancet* 344:1449, 1994). However, these effects are not permanent. Recurrence of angina following CABG surgery occurs in 3–20% of patients, and 31% will require repeat surgical or interventional cardiologic revascularization by year twelve (Weintraub et al., "Frequency of repeat coronary bypass or coronary angioplasty after coronary artery bypass surgery using saphenous vein grafts," *Am. J. Cardiol.* 73:103, 1994).

Before the CABG operation became accepted, various other methods were attempted to improve arterial inflow. Pedicle grafts of muscle and omentum were employed in the 1930's by Beck and O'Shaughnessy (C. Beck, "The development of a new blood supply to the heart by operation," *Ann. Surg.* 102:801, 1935; L. O'Shaughnessy, "An experimental method of providing a collateral circulation to the heart," *Br. J. Surg.* 23:665, 1935). In the early 1940's, Vineberg developed the technique for implanting a distally ligated internal mammary artery with its side branches not ligated into a bluntly created tunnel in the myocardium (A. Vineberg, "Coronary anastomosis by internal mammary implantation," *Can. Med. Assoc. J.* 78:871, 1958), with clinical application beginning in 1950. Murray et al. used the internal mammary artery experimentally as a pedicled bypass in 1954 (Murray et al., "Anastomosis of a systemic artery to the coronary," *Can. Med. Assoc. J.* 71:594. 1954). By the 1960's, experimenters were working on the techniques that matured into present-day aortocoronary bypass and segmental coronary artery bypass (Johnson et al., "Extended treatment of severe coronary artery disease," *Ann. Surg.* 170:460, 1969).

The technique for percutaneous transluminal angioplasty was introduced in the early 1970's by Gruentzig, initially for work in the peripheral vasculature. By 1978, he had applied this technique to the coronary arteries (A. Gruentzig, "Transluminal dilatation of coronary artery stenosis," *Lancet* 1:263, 1978). Although this procedure avoids the drawbacks of coronary artery surgery, it is limited by its own risks of abrupt vessel closure, incomplete revascularization at the time of the procedure, and restenosis. A restenosis rate of 30% is the average reported in the literature (M. Bevans and E. Mclimore, "Intracoronary stents: a new approach to coronary artery dilatation," *J. Cardiovascular Nursing* 7:34, 1992). Studies show that all arteries undergoing any type of intervention—balloon angioplasty, atherectomy, stent placement or laser balloon angioplasty—show similar restenosis rates at 6 months (Kuntz et al., "Novel approach to the analysis of restenosis after the use of three new coronary devices," *J. Am. Coll. Cardiol.* 19:1493, 1992). Other new technologies are undergoing evaluation for treatment of coronary artery disease, including various types of stents with different characteristics, low speed rotators, transluminal extraction catheters, laser angioplasty and adjunctive therapies. As yet, the problems of acute complications and restenosis remain unsolved.

In addition to the technical difficulties that beset surgical and cardiological interventions are their anatomical constraints: all these technologies are limited to macroscopic lesions in the larger coronary arteries. Although these interventions increase proximal arterial inflow when successful, this may not benefit myocardial tissue if there is extensive distal or small vessel disease. Furthermore, none of these techniques addresses the problem of ischemia at the tissue level which may result from uncorrected multivessel macrodisease, from uncorrected small vessel disease or from disease progression after successful revascularization.

To circumvent these anatomical constraints, techniques have been described to allow blood to enter the myocardium transmurally, directly from the ventricular cavity. Early techniques have focused on the placement of conduits from the ventricle into the myocardial wall (Goldman et al., "Experimental method of producing a collateral circulation to the heart directly from the left ventricle," *J. Thor. Surg.* 31:364, 1956; Massimo et al., "Myocardial revascularization by a new method of carrying blood directly from the left ventricular cavity into the coronary circulation," *J. Thor. Surg.* 34:257, 1957). More recently, techniques have been proposed that create channels into the myocardium, providing a supply of blood extravascularly (Mirhoseini et al., "Revascularization of the heart by laser," *J. Microsurg.* 2:253, 1981). None of these techniques directly connects with the local vascular system, depending instead on intramural diffusion into the myocardial sinusoids to supply tissue needs. None of these techniques, therefore, provides a method for small vessel or microvessel arterial revascularization within the myocardium.

SUMMARY OF THE INVENTION

Accordingly, it is an object of the invention to improve vascular inflow to ischemic muscle tissue. Revascularization at the level of the microcirculation would serve to complement or supplement existing macrovascular techniques (e.g., peripheral vascular bypass, CABG and PTCA) for increasing arterial inflow.

It is a further object of the invention to stimulate angiogenesis within muscle tissue.

It is yet another object of the invention to improve the balance between muscle tissue oxygen supply and oxygen demand by improving small vessel circulation and microcirculation through stimulation of local intramuscular angiogenesis.

Other objects of the invention will, in part, be set forth below and, in part, be obvious to one of ordinary skill in the art given the following description.

The invention includes, inter alia, methods for treating muscle ischemia. In one embodiment, the invention described herein can be understood as methods for stimulating angiogenesis within muscle tissue. According to this practice, the method includes accessing the muscle with a delivery system, penetrating the muscle and using the delivery system so as to enclose within the muscle at least one body formed of a biocompatible material and dimensionally adapted for being enclosed within the muscle. A delivery system can include any system adapted for accessing a muscle. The delivery system, in one embodiment, can include a catheter. Access to the muscle can take place by guiding a catheter delivery system through the patient's vascular system. Once the muscle has been accessed, it can be penetrated. The delivery system then operates to enclose within the muscle at least one body formed of a biocompatible material and dimensionally adapted for being enclosed within the muscle.

The method can include stimulating angiogenesis by enclosing within the muscle a body that is of an appropriate size and shape to be implanted within the designated muscle. The delivery system can operate to enclose the body in the muscle by substantially sealing the body within the muscle. In one embodiment, penetrating the muscle can include driving the distal portion of the delivery system into the muscle. Penetrating the muscle can include driving the biocompatible body into the muscle. The delivery system is adapted for enclosing at least one biocompatible body within the muscle. Alternatively, the delivery system can be adapted for implanting a plurality of bodies in muscle tissue. In one embodiment, the delivery system is adapted for delivering into the muscle an agent for promoting angiogenesis. An agent capable of promoting angiogenesis can include any substance whose biological effects include stimulating the growth and development of blood vessels.

Angiogenesis, as the term is used herein, is understood to be those processes of forming or developing blood vessels in a tissue. It is understood that angiogenesis is promoted through contact of the surfaces of said body with the muscle tissue. Accordingly, a body can be any three dimensional structure with surfaces that contact the muscle tissue. It is desirable that the body described herein be made of materials compatible with the tissues of the human body, so that the materials do not incite toxic reactions. The term biocompatible, as used herein, refers to any material that does not incite toxic reactions. In one embodiment, the materials used for the implantable device can be conducive to thrombus formation. In this embodiment, the implantable device can have the effect of keeping patent a space within the muscle tissue surrounding the device so that blood pooling can take place adjacent to the device. However, any method conducive to thrombus formation can be used. Furthermore, any agent capable of promoting angiogenesis can be delivered into the muscle.

The term implant may be used to refer to certain embodiments of these devices, although this term is not intended to limit the scope of the descriptions that follow. Biocompatible materials can be made biostable or biodegradable, bioactive or inert, depending upon the selected composition. Biocompatible materials can include bioartificial polymeric materials, formed as a hybrid or composite of synthetic and biological polymers that thereby overcomes the lack of biocompatibility associated with certain synthetic polymers and enhances the mechanical properties of natural polymers. Biocompatible materials can include hydrogels, which are materials comprising water-swollen polymer networks. Conventional hydrogels change little in swelling with environmental conditions while stimuli-responsive hydrogels may swell or deswell, depending on changes in environment such as temperature, pH, ionic strength, electric field, chemical or biological agents, mechanical stress or radiation. Hydrogels may be biostable or biodegradable. Hydrogels can be combined with other biocompatible materials to make implants. Further descriptions of exemplary types of bodies are presented herein. Other embodiments and materials for manufacture will be apparent to those ordinarily skilled in the art.

One practice of these methods involves stimulating angiogenesis within the myocardium, although it is understood that these methods are not thereby limited but rather can be applied to any muscle tissue. According to this practice, the method can include the steps of accessing the myocardium, penetrating the myocardial wall of the heart, and releasing within the myocardial wall a device that stimulates angiogenesis. Myocardial access can be via a transepicardial or a transendocardial route. Access can be provided intraoperatively or transvenously. In one practice, the physician uses the transvenous, transendocardial route for access and, under fluoroscopic control, manipulates a catheter to the intended site for device implantation. In one practice of this method, penetration of the myocardium can be accomplished by the device that is to be implanted. In an alternative method, penetration can be accomplished by a catheter-directed mechanism that serves as a guidewire over which the device is implanted. Other methods for delivering the device into the myocardium will be apparent to those of ordinary skill in the art.

According to one method, the device implanted in the tissues of a muscle has been deformed before its insertion and dynamically tends to revert to its pre-deformation shape after it is implanted. Deformation can occur by the application of deforming stresses. Deforming stresses are those forces that alter the shape of a body, commonly by compression or extension. The native configuration of a body is the shape in which it exists in the absence of these deforming stresses. Dimensions that have been altered can vary in size or in shape. The implantable devices as described herein may be made of resilient or flexible materials. A flexible device can be characterized by its ability to be deformed. A device deformed prior to insertion can revert towards its pre-deformation shape after implantation. Alternatively, a device may be susceptible to deformation after implantation, either from the action of the contracting and relaxing muscle, as exemplified by the beating heart or from reaction to body heat, upon application of an activating agent, or by any other suitable means. Representative materials include metallics and plastics. Metallic materials include stainless steel, MP35N, Nitinol™, Elgiloy, and Titanium, materials with sufficient resilience to be employed to form flexible bodies. Plastic materials include polymers, for example silicone.

According to another method, the device implanted in the myocardium is made of a heat responsive material. A material that changes its shape in response to heat is termed a heat responsive material. In one embodiment, the implantable body changes its shape in response to intramuscular heat. Intramuscular heat can include that heat intrinsic to the muscle or that heat obtained from a source external to the muscle that is conveyed into the muscle's interior. Some heat responsive materials will return to a pre-selected shape in response to a change in thermal condition. These materials are termed thermal shape memory materials, an example of which is Nitinol™.

In one embodiment, the systems and methods produce biological reactions for purposes of stimulating angiogenesis. The methods described herein include those methods of promoting angiogenesis by implanting in a muscle tissue a body formed of a biocompatible material that incites an inflammatory reaction within the tissue of the muscle. It is understood that inflammation can be incited by the implantation of substances that trigger the inflammatory cascade to stimulate angiogenesis. The inflammatory cascade can be triggered by those processes related to wound healing and tissue repair. In certain embodiments, the methods described herein further include the implantation of devices that can produce blood coagulation by biochemical stimulation, and thereby form thrombus. An example of a device that produces blood coagulation by biochemical stimulation is a device that includes substances that trigger the coagulation cascade such as thrombin. Such biochemical substances can be imbedded in the structural material of the device, or can be carried on or affixed to its surfaces.

In one embodiment, angiogenesis can be stimulated by inciting local healing reactions in the muscle tissue. These local healing reactions are understood to trigger the inflammatory cascade and stimulate angiogenesis. Mechanical stimulus for inflammation is produced by the presence of a rigid or flexible device within muscle tissue that provides resistance to normal muscle contraction and relaxation. Mechanical stimulus for inflammation is also produced by a flexible body introduced into the muscle in a deformed state that has the inherent tendency to return to its native configuration. Such a body, as it reverts to its native configuration following implantation, applies a force to the surrounding tissues and is understood to provide thereby a mechanical stimulus for triggering inflammation.

One embodiment of the systems and methods described herein can include a kit for promoting angiogenesis. In one embodiment, the kit can include a delivery system for accessing a muscle, an implantable body dimensionally adapted for being enclosed within the tissues of the muscle, and an implantation device to insert the implant within the muscle.

In one embodiment, the systems and methods described herein include apparatus for promoting angiogenesis. In one embodiment, this apparatus has at least one surface carrying a substance capable of promoting localized angiogenesis. As one embodiment, this apparatus can include an implant formed of a biocompatible material that has a drug releasing compound affixed to at least one of its surfaces. The surface carrying the substance capable of promoting localized angiogenesis can be coated with said substance or can be made of a material that comprises said substance. The substance capable of promoting localized angiogenesis can be a drug releasing compound. The term drug releasing compound as employed herein will be understood to include any substance that conveys a pharmacological or therapeutic agent. The drug releasing compound can include a pharmacological agent combined with an appropriate vehicle, or alternatively, the drug releasing compound may entirely consist of a pharmacological agent. One example of a drug releasing compound is the coagulation factor thrombin. In one embodiment, this apparatus can have at least one drug releasing compound affixed to the implantable device beneath a timed release coating. Alternatively, the drug releasing compound can be admixed with a timed release agent. In an alternate embodiment, the implantable device is entirely made of a drug releasing compound.

In yet another embodiment, the device is designed to contain an internal reservoir into which can be placed a drug releasing compound that is able to diffuse through the wall of the device. The reservoir can be constructed as an empty cavity within the device to be filled with a drug releasing compound. In this embodiment, the device is made of a material that is specifically permeable to the drug releasing compound within it, so that the contained drug can penetrate the device and contact the surrounding tissue. Alternatively, the drug releasing compound can be contained within the lumen of a spring, to be released between the spring coils as the heart contracts, or the compound can be formulated as a gel or resin that is deployed between the coils of the spring, to be released into the tissues with myocardial contraction.

In another embodiment, the implantable device includes a radiation source. A body made of a biocompatible material can be made to deliver localized amounts of radiation to surrounding tissues by incorporating a radiation source. The radiation source can be affixed to a surface of the implantable device. Alternatively, the radiation source can be carried within the implantable device. In yet another embodiment, the radiation source can be incorporated into the material employed to form the implantable device. When a bioceramic material such as glass is used to form the implanted device, radioactivity present within the implantable body will degrade the glass and dissolve it in time, resulting in biodegradation.

Not to be bound by theory, nonetheless it is understood that angiogenesis may be promoted by causing blood to pool in a localized area and the pooling of blood is understood to result in thrombus formation with the subsequent stimulation of angiogenesis. Accordingly, in one embodiment, the system described herein provides an implantable body that includes a surface that allows blood to pool. This surface may be on the external or the internal aspect of the device. In one embodiment, the surface of the device may provide at least one concave area in which blood can pool. The external face may have a projection that imbeds itself into the muscle tissue and prevents normal muscle contraction or relaxation. The action of the projection upon the muscle tissue during a cycle of muscle contraction and relaxation results in the creation of lacunae within muscle that become filled with pooled blood.

In one embodiment, the devices described herein include a flexible structure. Flexible materials may be arranged in a variety of shapes, including springs and bellows. The springs can comprise a regularly coiled filament of a metal or plastic material arranged in a tubular shape. In other embodiments the spring is arranged in alternative geometries, each of which provides a deformable resilient body. The term tubular will be understood to include any shape defined by a sidewall that includes at least two openings with a space extending therebetween, and wherein the sidewall can be generally cylindrical, rectangular, triangular or any other suitable shape. A bellows device is able to be compressed and to be expanded as it is acted upon by the myocardium. A bellows may enclose a cavity having drug-releasing compounds contained therein and optionally the bellows may include a port for releasing the compound from the cavity upon compression and expansion of the bellows. Blood pooling can take place within the lumen of the spring, thereby to stimulate angiogenesis. The spring may be close-wound, such that adjacent coils are in contact, or the spring may be open pitch with a space between adjacent coils.

In one embodiment, the biocompatible body comprises a heat responsive material. This term is understood to include thermal shape memory or superelastic materials. In an alternative embodiment, the biocompatible body comprises a rigid material. The implantable devices described herein can include rigid materials that are sufficiently stiff to prevent or reduce deformation of the implantable device. A rigid material can resist deforming stresses such as those produced by muscle contraction. Rigid materials can be bioabsorbable, subject to local degradation and resorption over time. Representative materials include metallics and plastics. Metallic materials include stainless steel, MP35N, Nitinol™, Elgiloy, and Titanium. Plastic materials include Teflon, polymethyl methacrylate (PMMA) and bioabsorbable materials such as Polyglycolide (PGA) and Lactide Polylactide (LPLA). Biocompatible materials conforming to these definitional parameters are well-known in the art of biomedical engineering and any suitable biomaterial, including polymers, metals, ceramics, carbons, processed collagen, chemically treated animal or human tissues, or bioabsorbable materials may be used.

In one embodiment, the apparatus can include a scaffold that supports tissue ingrowth. The scaffold can be a structural matrix of solid supporting elements that surround interstitial spaces. The interstitial spaces provide foramina for tissue ingrowth throughout the scaffold, and the supporting elements organize the arrangement of the tissue elements within the scaffold. Tissue growth factors deployed in the interstitial spaces or carried on or affixed to the supporting elements enhance tissue ingrowth and angiogenesis. Tissue growth factors are agents that act to initiate or accelerate the processes of tissue proliferation. Examples of tissue growth factors include Fibroblast growth factor (FGF) types I and II, and vascular endothelial growth factor (VEGF).

In one embodiment, the devices can be substantially solid scaffolding, with relatively small channels provided within this solid material to permit and organize tissue ingrowth. This embodiment can be configured to enclose a space within it into which tissue can grow. Apertures in the solid body are openings that permit tissues to grow into the interior cavity. The cavity may be entirely enclosed by solid walls on all sides, with apertures providing the route for tissue ingrowth. Alternatively, the device may be tubular in shape with at least one sidewall removed, so that the internal cavity is in communication with the milieu external to the device. In another embodiment, the scaffold can include channels extending through the biocompatible body to support tissue ingrowth.

Other aspects and embodiments of the invention will be apparent from the following description of certain illustrative embodiments.

The invention provides systems and methods for promoting angiogenesis in muscle tissue. These systems can be employed for treating ischemia caused by acute or chronic circulatory insufficiency, for example, arterial occlusions or compartment syndromes. For purposes of clarity, the system and methods of the invention will now be described with reference to treating ischemia within the myocardium. However, it will be understood that the system and methods of the invention are not to be restricted to application within the myocardium, but rather can be applied to any muscle of the body, and that these applications of the system and methods of the invention in muscle tissue will be apparent to those of ordinary skill in the art from the following description of the illustrated embodiments.

BRIEF DESCRIPTION OF THE DRAWINGS

For a better understanding of the invention together with the objects, advantages and capabilities thereof, reference is made to the accompanying drawings in which like reference numbers refer to like elements:

FIG. 6b depicts a cross-sectional view of the embodiment shown in FIG. 6a.

FIGS. 7a–7e illustrate one practice of implanting bodies within the myocardium to promote angiogenesis.

DETAILED DESCRIPTION OF ILLUSTRATED EMBODIMENTS

The invention includes, inter alia, methods for treating symptoms of muscle ischemia by stimulating local angiogenesis and thereby increasing the availability of oxygenated blood at the tissue level. In one embodiment, these systems and methods can be applied to the ischemic myocardium. Inadequate myocardial perfusion can persist at the tissue level despite revascularization techniques in the coronary system that increase the total amount of arterial inflow. By stimulating angiogenesis, the systems and methods described herein improve the delivery of oxygenated blood to the heart muscle. This, in turn, can lead to an improvement of pathological conditions attributable to myocardial ischemia, including angina, infarction and pain.

Figure 1A:
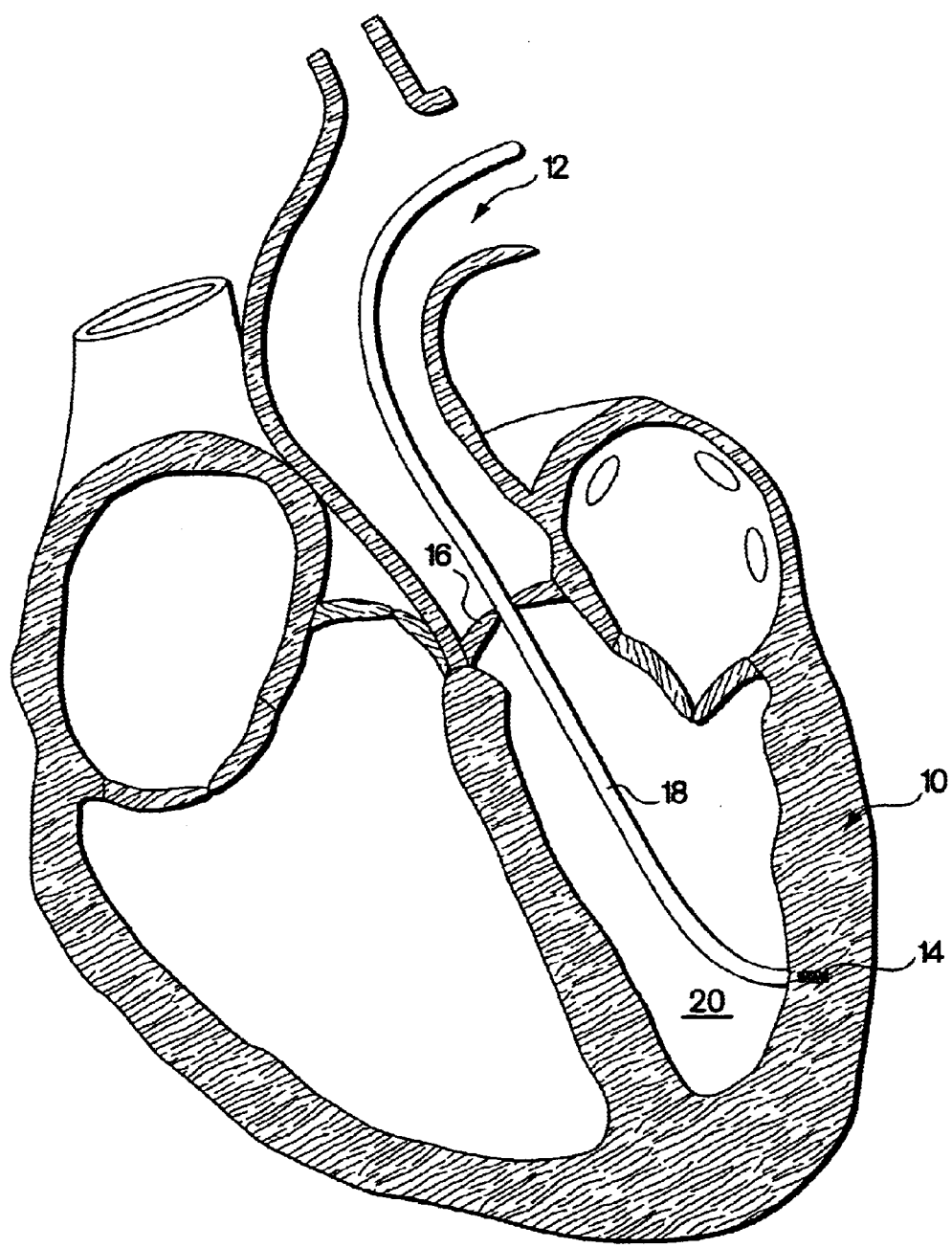
FIG. 1a depicts an anatomical cross-section diagram of the heart with a catheter positioned within the left ventricle and a body disposed within the cardiac muscle for stimulating angiogenesis.

FIG. 1a illustrates one embodiment of an implantable device capable of promoting angiogenesis in muscle tissue, depicted here as implanted within the myocardium. Specifically, FIG. 1a depicts in cross-section the myocardium 10, the aorta 12, an implantable body 14, the aortic valve 16 and a delivery system 18. As illustrated in FIG. 1a, the body 14 can be placed within the myocardium 10, wherein the body 14 fits between the endocardium and epicardium, to be contained fully within the myocardial wall.

FIG. 1a further shows that the delivery system 18 can be passed through the aorta 12 and the aortic valve 16 into the chamber of the left ventricle 20, thereby providing access to the myocardium 10. The delivery system 18 is typically a catheter that has been adapted for the delivery of the body 14 into the myocardium 10. The technique for introducing the delivery system 18 into the aorta 12 is well-known to those skilled in the art. Percutaneous arterial puncture of a distal artery allows access to the arterial system. Femoral or brachial arteries are commonly selected. After intra-arterial access is accomplished, the delivery system 18 is threaded proximally until the aorta 12 is reached. Progress of the catheter through the great vessels is monitored fluoroscopically. Once the left ventricular chamber 20 is reached, the delivery system 18 is directed towards the segment of myocardium 10 where the implantable device 14 is to be delivered. The delivery system 18 is positioned within the left ventricle 10 using techniques well-known in the art. The appropriate segment of the endocardium is identified, with care taken to avoid trauma to the papillary muscles or intraventricular trabeculations. While the embodiment illustrated in FIG. 1a shows the left ventricle 20 being accessed with the delivery system 18, placement is not limited to the left ventricle 20, as would be apparent to a practitioner of ordinary skill in the art. Transvenous introduction of the delivery system provides access to the right ventricular wall and the interventricular septum if clinical conditions warrant implantation of the device within these myocardial structures. Methods for introduction of the implantable body 14 into other muscles will be apparent to practitioners skilled in the art.

The embodiment of the system for promoting intramuscular angiogenesis that is illustrated in FIG. 1a comprises a body 14 that is of appropriate size to fit between the walls of the myocardium 10. Dimensions of the myocardium are different at different anatomical locations, and can change dynamically with contraction and relaxation. Furthermore, there is physiological and pathological variability to myocardial thickness. Hypertrophy of the myocardium occurs with increasing myocardial work, for example, in hypertensive patients. Thinning of the myocardium occurs with ischemic injury, seen most extremely with ventricular aneurysm formation. In this embodiment, dimensions of the body 14 are selected to fit within the myocardial region where it is implanted. A standard size can be used under routine circumstances, although variations of dimensions to correspond with specific anatomic needs are possible. Techniques for measuring myocardial thickness are known to practitioners of the art, allowing customization of implantable devices in accordance with the particular dimensions measured in a patient. Implantable bodies 14 can also be selected in dimensions adapted for intramuscular placement at any anatomic site.

The depicted body 14 is made of a biocompatible material. Biocompatibility, as understood for these systems and methods, is understood to describe, inter alia, a characteristic of a material wherein there are no or limited toxic reactions to the materials of which the device is composed, although the material can be thrombogenic and can elicit a foreign body reaction. A foreign body reaction is a form of a nonimmune inflammatory response with an infiltrate predominately composed of macrophages. Since the body 14 is made of a biocompatible material, if it elicits an immunological reaction characterized by antibody formation, such a reaction is understood not to result in local, distant or systemic pathological effects. Biocompatible materials conforming to these definitional parameters are well-known in the art of biomedical engineering and any suitable biomaterial, including polymers, metals, ceramics, carbons, processed collagen, chemically treated animal or human tissues, or bioabsorbable materials may be used. Biocompatible material can be made biostable or biodegradable, bioactive or inert, depending upon the selected composition. Biocompatible materials can include bioartificial polymers formed as a hybrid or composite of synthetic and biological polymers fabricated to overcome the lack of biocompatibility associated with certain synthetic polymers while enhancing the mechanical properties of natural polymers.

Biocompatible materials can include hydrogels, which are materials comprising water-swollen polymer networks. Conventional hydrogels change little in swelling with environmental conditions while stimuli-responsive hydrogels may swell or deswell, depending on changes in environment such as temperature, pH, ionic strength, electric field, chemical or biological agents, mechanical stress or radiation. Hydrogels may be biostable or biodegradable. Hydrogels can be combined with other biocompatible materials to make implants. A body made of a biocompatible material can be made to deliver localized amounts of radiation to surrounding tissues by incorporating a radiation source. When a bioceramic material such as glass is used to form the implanted device, radioactivity present within the implantable body will degrade the glass and dissolve it in time, resulting in biodegradation. Biocompatible materials include porous materials. Porous materials contain passages or channels that permit the passage of fluids or particulate matter. Porous materials include open pore structures and closed pore structures. Open pore structures are those materials that permit fluids to move from one surface to an opposing surface in the material through a convoluted pathway of interconnecting networked channels. Closed pore structures are those materials in which the pathways or channels are blocked so that fluid is not afforded a continuous and interconnected network of channels to move from one surface of the material to an opposing surface.

Figure 1B:
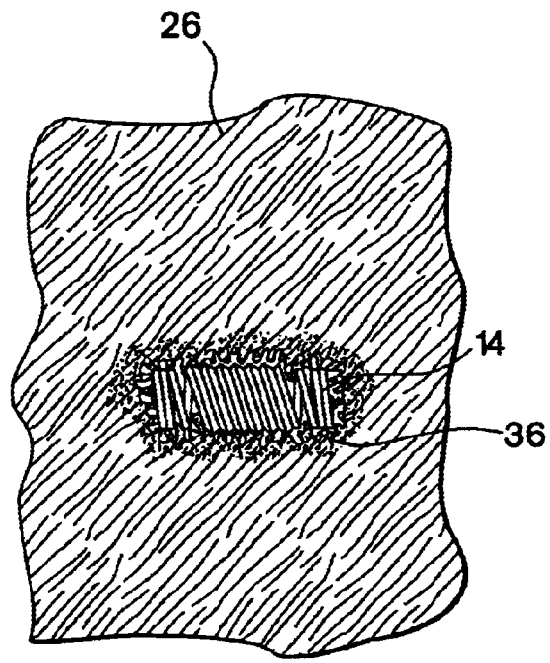
FIG. 1b depicts in more detail the position of a body located within the tissue of a muscle causing blood pooling.
Figure 1C:
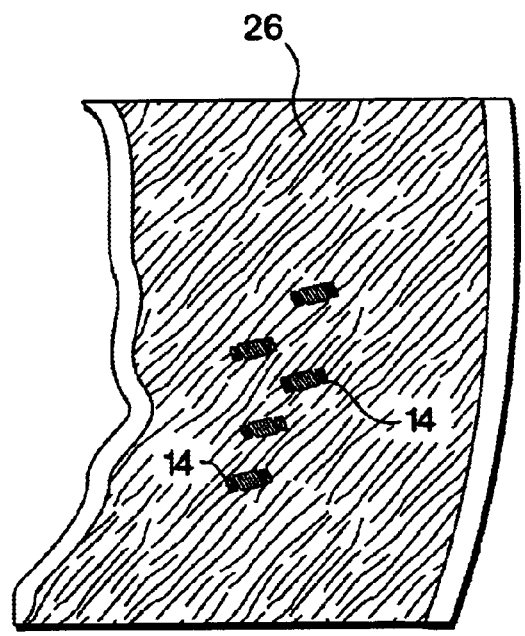
FIG. 1c depicts a pluralities of bodies disposed within the tissue of a muscle for stimulating angiogenesis.

FIG. 1b shows in more detail the position of the implantable body 14 within the tissue of a muscle 26. Surrounding the body 14 are intramuscular cavities 36 within which blood can pool. With blood pooling, thrombus formation occurs. Coagulation proteins, complement products, platelets and other blood and tissue fluid products are understood to be involved in the interaction between pooled blood and a biocompatible implantable body 14. FIG. 1c depicts a plurality of implantable bodies 14 within the tissue of a muscle 26.

Figure 1D:
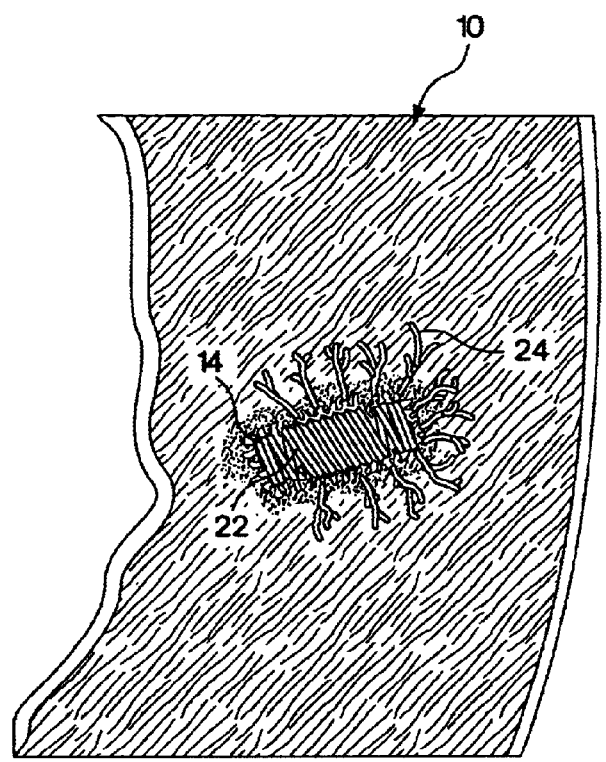
FIG. 1d depicts in more detail the position of a body located within the tissue of a muscle for stimulating angiogenesis.

FIG. 1d shows in more detail the position of the body 14 within the myocardium 10. It is understood that muscle tissue reacts to the implantation of this body 14 by processes of angiogenesis and neoangiogenesis. It is further understood that for most biomaterials implanted into solid tissue encapsulation by a relatively thin fibrous capsule composed of collagen and fibroblasts ultimately occurs. An ongoing inflammatory infiltrate consisting of monocytes/macrophages and foreign body giant cells may also occur, indicating persistent tissue irritation. Varying degrees of foreign body reaction are understood to occur with different biocompatible materials. Representative polymers provoking inflammation include polyethylene terephthalate, polyglycolic/polylactic acid, polycaprolactone and polyhydroxy butyrate valerate, although other materials will be apparent to those skilled in the art. Concomitant with these inflammatory processes, there is a localized proliferation of blood vessels 24 adjacent to the external surface 22 of this body 14. The implantable body 14 can have a coating of a drug containing or releasing compound to provide for delivery of a therapeutic agent into the tissue, or to provide drugs that promote or aid angiogenesis or the implantable body can be entirely formed of such drug releasing compounds. The density of the coating on the device can also be controlled to improve radiopacity.

Figure 1E:
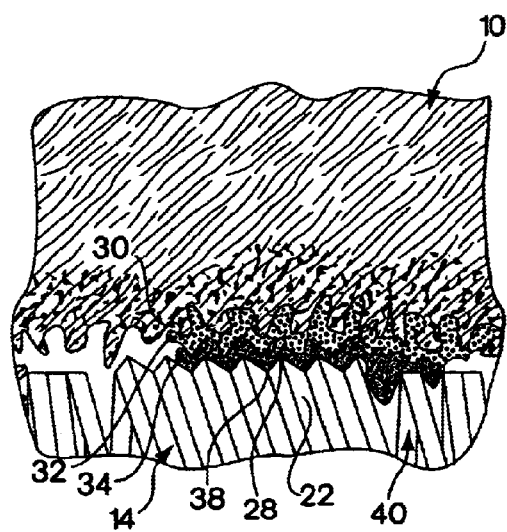
FIG. 1e depicts in more detail the interaction of a body positioned within the myocardial tissues creating intramyocardial cavities in which blood pooling and thrombus formation occur.

FIG. 1e shows in more detail one type of interaction between the body 14 and the myocardium 10. The external projections 28 of the body 14 may impede the motion of the implant, restraining it within the myocardium 10. Tearing or distortion of the filaments of the myocardium 10 result in the formation of intramyocardial cavities 30 surrounding the body 14. The space that is formed by these intramyocardial cavities 30 can be partially filled by pooled blood 32 which can culminate in thrombus formation 34. Coagulation proteins, complement products, platelets and other products are understood to be involved in the interaction between pooled blood 32 and a biocompatible body 14. The external surface 22 of the body 14 can provide nucleation sites for such thrombus formation 34 to occur. Thrombus formation 34 can occur in the absence of formation of intramyocardial cavities 30, with blood pooling 32 taking place on the concavities 38 formed by the external surfaces 22 of the apparatus of the invention. Alternatively, blood pooling 32 may occur on the internal face 40 of the body 14. Thrombus formation involves platelet adherence, activation and aggregation, with erythrocytes adsorbed onto the platelet plug thus formed.

Figure 2:
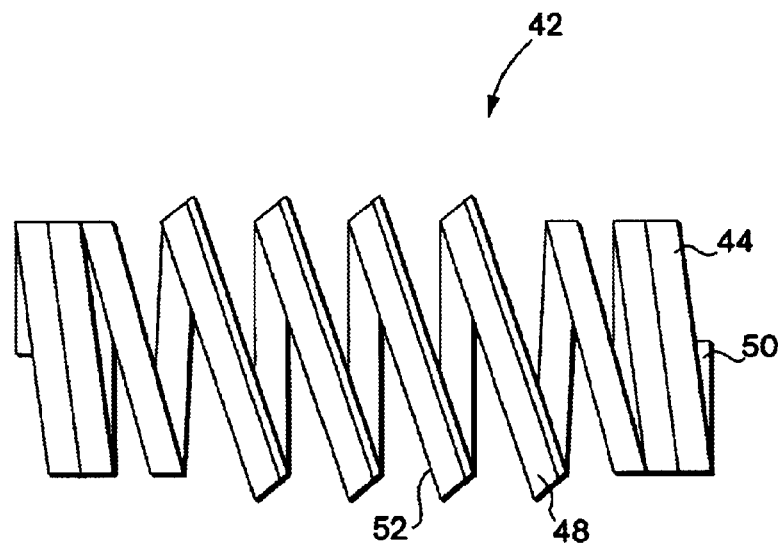
FIG. 2 depicts a device that has a flexible body.

FIG. 2 depicts one embodiment of an implantable body adapted for intramuscular implantation according to the systems and methods described herein configured as a flexible structure 42. The embodiment depicted in FIG. 2 includes two spring components, a close pitch spring 44 and an open pitch spring 48. In this embodiment, the two spring elements are made from a flat rolled strand of metal 50. The edges 52 of the open pitch spring 48 are angulated in this embodiment. Effective dimensions include a range of thickness to width from 0.002" to 0.005" by 0.008" to 0.018" in stainless steels, although the selection of aspect ratio may be even greater. Flat wire is typically rolled from a round geometry during the rolling procedure, producing a flat strand with curved edges. During fabrication of the flexible structure 42, a final edge dressing may be applied to improve the sharpness of the edges. Varying degrees of axial flexibility can be attained to correspond to the specifications of the delivery device. Different degrees of flexibility may be appropriate for placement in muscles in different anatomic areas. For example, within the heart muscle, a more rigid device may be more suitable for implantation in the apical myocardium, while a more flexible device may be more appropriate for implantation in the free ventricular wall.

The preferred embodiment of the flexible structure 42 is fabricated as a canted helical spring by winding 0.005"× 0.015" 316 stainless steel ribbon on a specially prepared mandrel. This mandrel is machined with 0.032" diameter barrels spaced approximately 0.2" apart. Between these two sections is a thread-like spiral with a 0.034" diameter root. The winding side of the thread is approximately 40 degrees to the perpendicular. The flexible structure 42 in the preferred embodiment is prepared by winding the ribbon along the axis of the mandrel with approximately two to three pounds of tension, beginning on the flat section, continuing along the threaded spiral and ending along the opposite flat. The wound device is then removed by carefully rotating the device to unthread it from the mandrel. Axial stretching may be necessary to size the device to the appropriate final length. The flat coils are trimmed, providing approximately 1.5 to 2 coils. As a final step, the distal flat coil is dressed with 600 grit-wet sandpaper creating a less blunt leading edge to minimize the insertion forces to embed the device. As finished, the overall length is approximately 0.28" and the maximum diameter is 0.06". Approximately 7 coils at a 40 degree angle to the perpendicular axis provide both an anchor and a porous design to permit blood to enter the cavity as well as partial ingrowth of the muscle tissue.

For example, the device described herein can be formed of alternate materials, including heat responsive materials such as Nitinol™, which can allow devices, or portions of devices, to change shape once implanted, such as by raising projections that more securely hold the body within the myocardium. Additionally, the devices described herein can be coated with or can carry drugs. In still other embodiments, the devices can be formed of a mesh material that facilitates tissue in growth. Still other variations, substitutions, additions and modifications can be made without departing from the scope of the invention.

It is understood that one advantage of the flexible structure 42 is the maximization of surface area of the device in contact with the tissues, thereby maximizing the volume of tissue responses. The flexible structure 42 illustrated in this figure shows one embodiment capable of maximizing this surface area. In this embodiment, the muscle is understood to herniate between the coils of the flexible structure 42. Other embodiments that maximize the surface area of the implantable body and thereby maximize contact of the device with the tissues can be fabricated by those skilled in these arts without departing from the scope of the systems and methods described herein.

Figure 3:
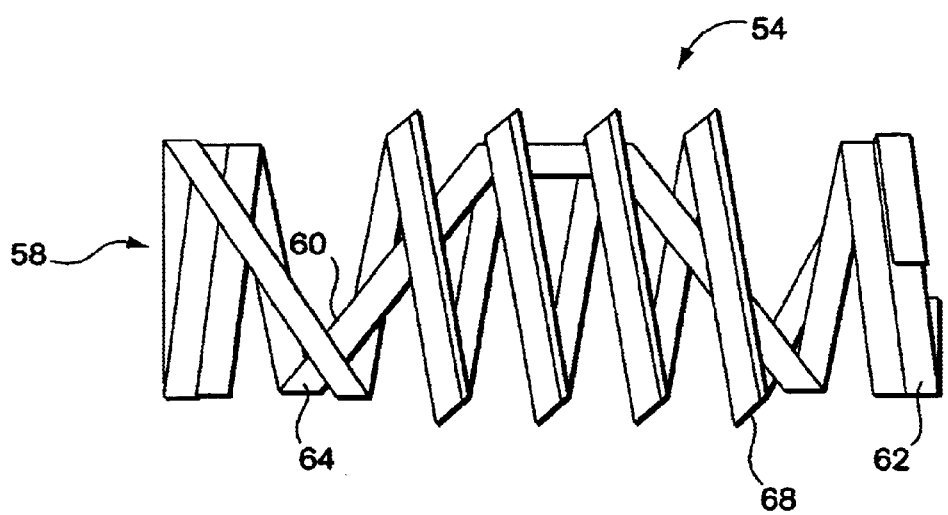
FIG. 3 depicts a device configured as a double helix spring.

FIG. 3 depicts an alternative embodiment of an implantable body adapted for intramuscular implantation according to the systems and methods described herein configured as a double helix spring 54 that encloses a lumen 58. This spring 54 has an inner helical structure 64 with an open pitch section 60 and a tighter pitch section 62. Surrounding this inner helical structure 64 is an outer helix 68 in an open pitch configuration.

Figure 4:
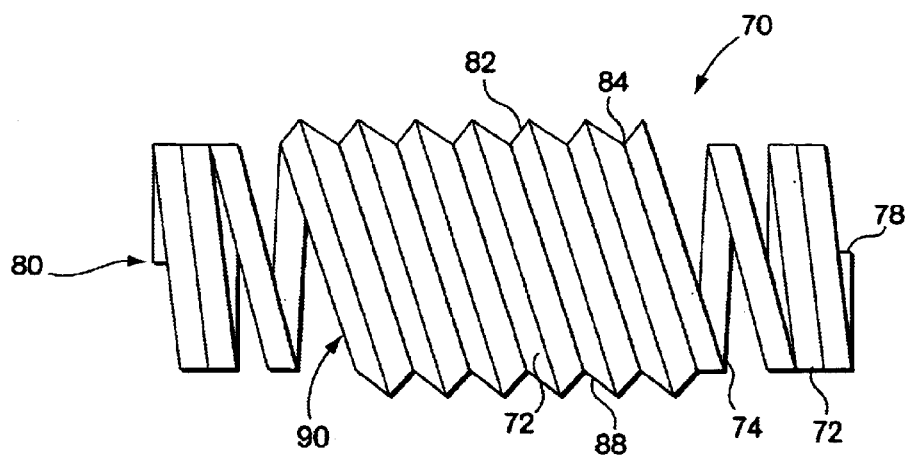
FIG. 4 depicts an alternative embodiment of an implantable body adapted for intramuscular implantation.

FIG. 4 depicts an alternative embodiment of an implantable body adapted for intramuscular implantation according to the systems and methods described herein configured as a flexible structure 70 comprised of a plurality of tighter pitch spring sections 72 connected by two open pitch spring elements 74. The flexible structure 70 is made of a continuous strand of flat rolled metal 78, enclosing a lumen 80. The canted edges 82 of the inner tighter wound spring sections 72 provide a series of concavities 84 on the external surface 88 that can provide pockets for blood to collect. Alternatively, there can be surfaces disposed on the internal face 90 of this flexible structure 70 that provide sites for blood to collect and coagulate. A device such as that depicted in FIG. 4 may be made of rigid or flexible materials.

Figure 5A:
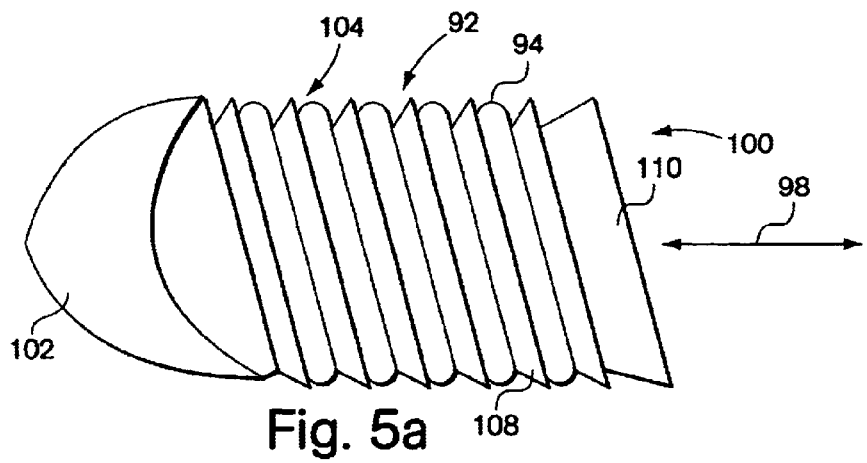
FIG. 5a depicts an embodiment having bellows formed into the body.
Figure 5B:
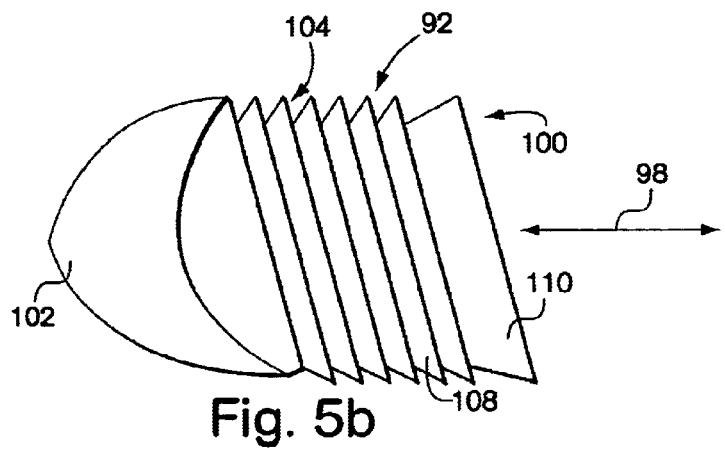
FIG. 5b depicts the bellows of FIG. 5a in a contracted form.

FIG. 5a shows an embodiment of a device for implantation into a muscle that is configured to include bellows 92. Bellows 92 is commonly a tubular structure with flexible sidewalls 94 made out of a solid material that responds to stresses applied along the longitudinal axis 98 by compressing and extending lengthwise. As illustrated, the bellows 92 of FIG. 5a is shown in an elongated state. FIG. 5b shows the same bellows 92 in a contracted state, with a reduced length. The bellows 92 contains a central lumen 100 into which can be dispersed various materials, including drug releasing compounds. The mechanical motion of the bellows 92 would then result in the expulsion of the drug releasing compounds from its lumen 100. FIG. 5a illustrates an embodiment of a bellows 92 having an anterior solid metal obturator head 102 and a flexible metal cylinder 104 attached to it. The flexible metal cylinder 104 may be configured as a series of annular ripples 108 to permit flexion and extension of the device at specific locations along its length. The annular ripples 108 can pleat and unpleat in an accordion-like manner in response to axially directed stress. In continuity with the flexible metal cylinder 104 and the flexible annular ripple 108 is a terminal posterior cuff of deformable metal foil 110.

Figure 6A:
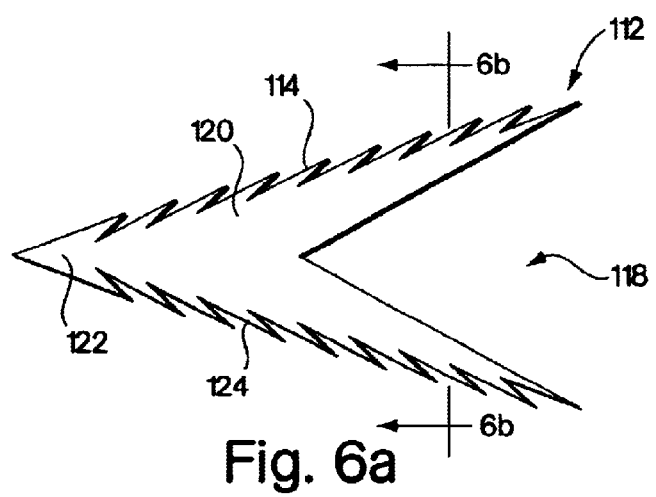
FIG. 6a depicts an embodiment comprising a rigid body adapted for penetrating a muscle.
Figure 6B:
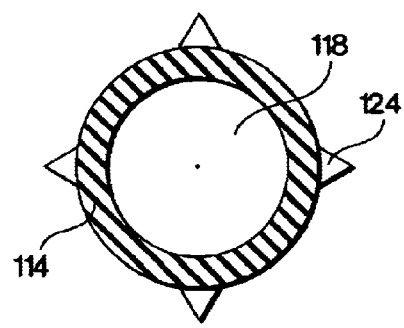
Figure 6C:
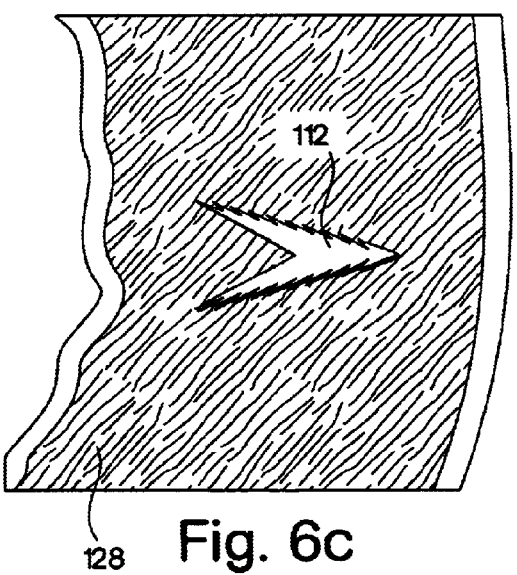
FIG. 6c depicts the embodiment of FIG. 6a positioned within the tissues of a muscle.

FIG. 6a depicts an alternative embodiment of an implantable body, and provides a longitudinally sectioned view of a cone-shaped body 112 made of rigid materials including a nondeformable housing 114 surrounding a central tapered cavity 118. The cavity ends before the distal tip 120 of the cone shaped body 112 so that the distal tip 120 is a solid, cone-shaped structure that culminates in an acutely angulated insertion point 122. The external surface of the body 112 has a series of exterior barbs 124. FIG. 6b shows a cross-sectional view of this embodiment illustrating the nondeformable housing 114, the central cavity 118 and the exterior barbs 124. These exterior barbs 124 may be arrayed circumferentially around the device, aligned in rows, disposed on the surface of the housing 114 in a helical pattern or in any other pattern. The exterior barbs 124 secure the body 112 in the muscle 128 at the location where it was disposed by the physician, as shown in FIG. 6c. This quill-like configuration, although adaptable for insertion in any muscle, is well adapted for the method of the invention described hereinafter with reference to FIGS. 7a, 7b, 7c, 7d, 7e.

Figure 7E:
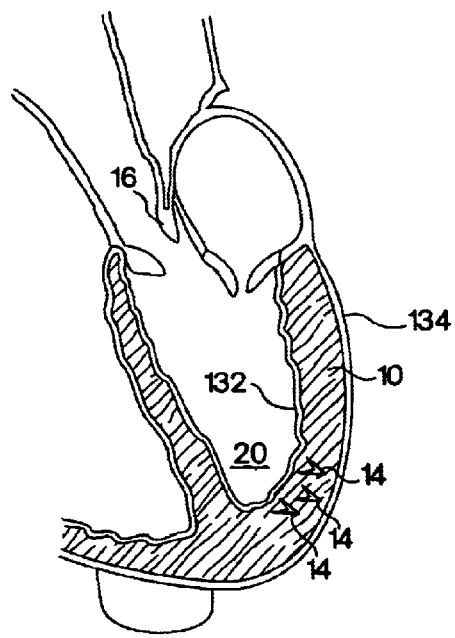

FIGS. 7a, 7b and 7c illustrate steps for a practice of one method of the invention. FIG. 7a shows a delivery system 18 being positioned in the left ventricle 20 across the aortic valve 16. The myocardium 10 is accessed by the delivery system 18. This figure shows the transendocardial route of accessing the myocardium 10, whereby the delivery system 18 transgresses the endocardium 132. Alternatively, an access route across the epicardium 134 is available if a transthoracic approach is chosen. Transepicardial access may take place at the time of a surgical procedure when the epicardium 134 is directly visualized. Alternatively, thoracoscopic techniques may permit transepicardial access. Once the myocardium 10 has been accessed, it is penetrated and the implantable device 14 is inserted within its tissues, as shown in FIG. 7b. Penetration into the myocardium 10 requires aligning the endocardial surface 132 with the distal end of the delivery system 18, then advancing the body 14 into the tissues of the myocardium 10, as shown in more detail in FIG. 7c. Thereafter, withdrawal of the delivery system 18 then occurs in the standard manner, as shown in FIG. 7d. One practice of this method requires repositioning the delivery system 18 within the left ventricular chamber 20 after it is withdrawn from the myocardium 10 so that another body 14 can be deposited within the myocardium 10. After the intended number of bodies 14 are positioned in the myocardium 10, the delivery system 18 is withdrawn as shown in FIG. 7d. FIG. 7e illustrates that multiple bodies 14 can be placed within the myocardium 10.

Figure 8:
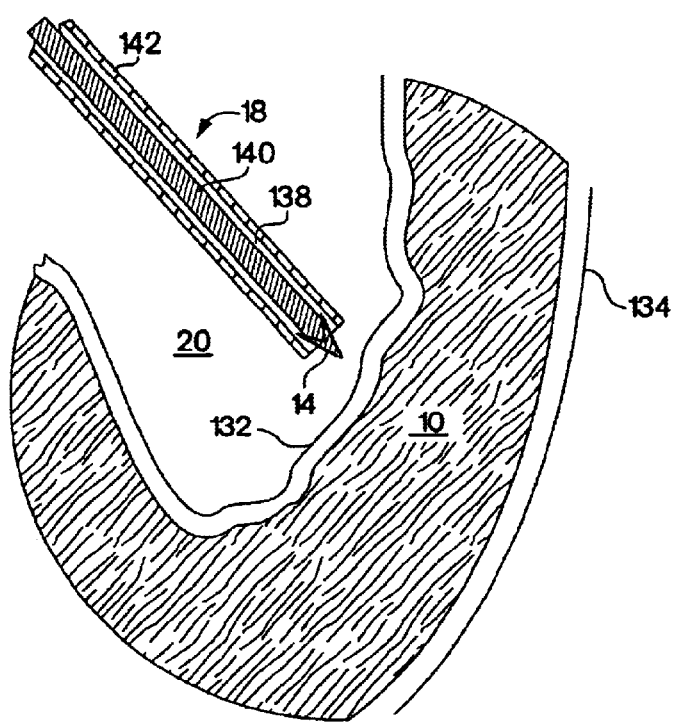
FIG. 8 depicts a cross-sectional view of an embodiment of a delivery system for placement of the implantable body within the myocardium.

FIG. 8 shows a cross-sectional view of an embodiment of the delivery system 18. In this embodiment, a delivery device 140 passes through the lumen 138 of a positioning catheter 142 to allow contact of the implantable body 14 with the myocardium 10. Once the positioning catheter 142 reaches the surface of the myocardium 10 by passage through the left ventricular chamber 20, the implantable body 14 is delivered through the epicardium 134 into the myocardial tissue 10. The delivery system 18 may contain within it a mechanism for positioning the body 14 within the myocardium 10. Alternatively, the body 14 itself may be located at the distal tip of the delivery system 18 and thereby provide the means for myocardial penetration, as shown in FIG. 8. One suitable delivery system 18 includes a catheter system that includes an injection mechanism mounted at its distal end operated under the control of an activator disposed at the proximal end and manipulated by the treating physician. The activator can cause the distal end of the delivery device 140 to penetrate the endocardium 132 and can cause the body 14 to be driven from the catheter and into the tissue of the myocardium 10. In one embodiment, wherein the delivery system 18 can deliver myocardial implants such as those depicted in FIGS. 6a–6b, the activator of the delivery system 18 can drive the implant from a chamber or catheter lumen, so that the pointed end of the implant pierces the tissue wall and the implantable body 14 passes into the myocardium 10. Other delivery systems can be employed without departing from the scope of the invention.

Figure 9A:
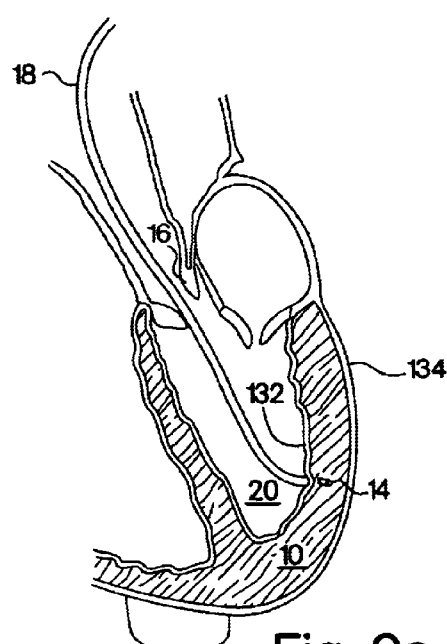
FIGS. 9a–c illustrate a practice of implanting bodies in a deformed configuration within a muscle.
Figure 9B:
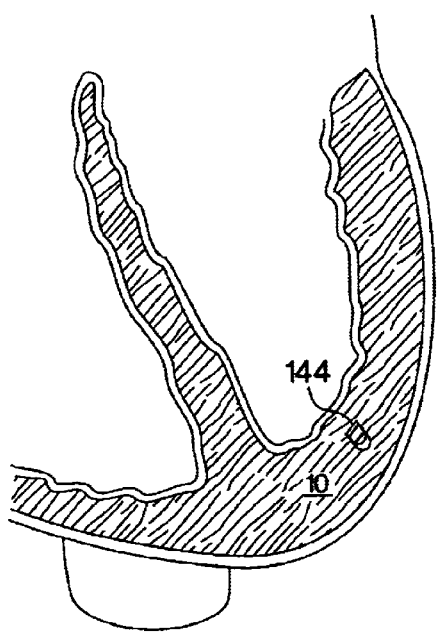
Figure 9C:
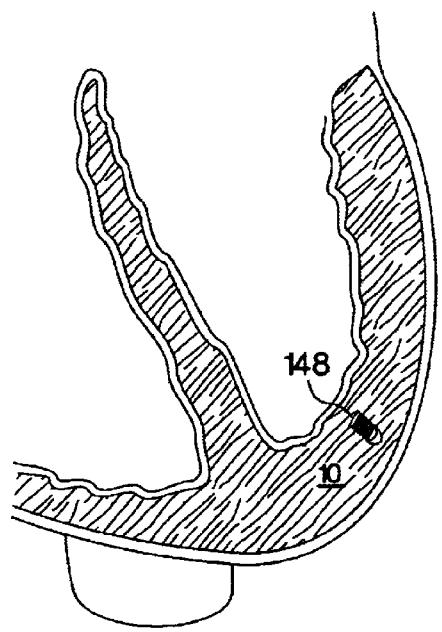

FIG. 9a illustrates another method of promoting angiogenesis within muscle tissue, here illustrated by depicting the method as employed in the myocardium 10. In FIG. 9a, a delivery system 18 is shown crossing the aortic valve 16 and the left ventricle 20 to gain access to the myocardium 10 by penetrating the endocardium 132. This figure shows a body 14 implanted in the myocardium 10 using the delivery system 18. FIG. 9b shows in more detail the deformed configuration 144 of this structure, while FIG. 9c shows the native configuration 148 of the structure within the myocardium 10. A practice according to this method involves inserting the body 14 in its deformed configuration 144 and relying upon its innate physical characteristics to restore it to approximately its native configuration 148. This process can take place because of the elastic memory of the body 14. Alternatively, a change in shape in the body 14 can occur because the body 14 is comprised of a thermal shape memory material.

Although the present invention has been described with reference to preferred embodiments, workers skilled in the art that changes may be made in form, detail and technique without departing from the spirit and the scope of the invention. Accordingly, the systems and methods of the invention are not to be limited by any of the above descriptions, which are provided to enable one to make and use the invention. Rather, the systems and methods of the invention are to be understood from the language of the claims below, which are to be interpreted as broadly allowed under the law.

We claim:

1. An apparatus for promoting angiogenesis comprising:

a flexible body formed of a biocompatible material and being dimensionally adapted for implantation within tissue of a muscle wherein said flexible body comprises a bellows for expanding and contracting responsive to muscle relaxation and contraction wherein said body defines a lumen that is adapted to maintain an open cavity in the tissue sufficient to permit blood pooling and external projections configured to create cavities between the tissue and the body to thereby stimulate angiogenesis.

2. An apparatus according to claim 1 wherein the projections are defined by annular ripples of the bellows.

3. An apparatus according to claim 1 further comprising at least one port in the body open to the lumen.

4. An apparatus according to claim 1 further comprising a drug releasing compound retained by a surface of the device.

5. An apparatus according to claim 4 wherein the drug releasing compound is contained within a lumen of the body.

6. An apparatus according to claim 4 wherein the drug releasing compound is applied to a surface of the device by a coating.

7. An apparatus according to claim 4 wherein at least a portion of the body is formed from a drug releasing compound.

8. An apparatus according to claim 3 wherein a drug releasing compound contained within the lumen of the body diffuses through the port during compression of the bellows.

9. An apparatus according to claim 1 further comprising a radiation source carried by the body.

* * * * *

UNITED STATES PATENT AND TRADEMARK OFFICE
CERTIFICATE OF CORRECTION

PATENT NO. : 6,692,520 B1
DATED : February 17, 2004
INVENTOR(S) : Gambale et al.

It is certified that error appears in the above-identified patent and that said Letters Patent is hereby corrected as shown below:

<u>Title page,</u>
Item [56], References Cited, U.S. PATENT DOCUMENTS, add the following:
-- 6,197,324 B1    03/2001    Crittenden
   6,248,112 B1    06/2001    Gambale et al.
   6,251,418 B1    06/2001    Ahern et al.
   6,277,082 B1    08/2001    Gambale
   6,447,522 B1    09/2002    Gambale et al.
   6,458,092 B1    10/2002    Gambale et al. --

Signed and Sealed this

Sixteenth Day of November, 2004

JON W. DUDAS
*Director of the United States Patent and Trademark Office*